US00PP16769P2

(12) United States Plant Patent
Warren

(10) Patent No.: US PP16,769 P2
(45) Date of Patent: Jul. 4, 2006

(54) RED MAPLE TREE NAMED 'FRANK JR.'

(50) Latin Name: *Acer rubrum*
Varietal Denomination: Frank Jr.

(75) Inventor: Keith S. Warren, Gresham, OR (US)

(73) Assignee: J. Frank Schmidt & Co., Boring, OR (US)

( * ) Notice: Subject to any disclaimer, the term of this patent is extended or adjusted under 35 U.S.C. 154(b) by 90 days.

(21) Appl. No.: 11/083,834

(22) Filed: Mar. 16, 2005

(51) Int. Cl.
*A01H 5/00* (2006.01)

(52) U.S. Cl. ..... Plt./224
(58) Field of Classification Search ..... Plt./224
See application file for complete search history.

*Primary Examiner*—Anne Marie Grunberg
*Assistant Examiner*—June Hwu
(74) *Attorney, Agent, or Firm*—Klarquist Sparkman LLP

(57) ABSTRACT

A variety of Red Maple which combines an upright pyramidal form with a distinctly straight central leader, unusually dark summer foliage, bright red fall color.

8 Drawing Sheets

Latin name of the genus and species of the plant claimed: *Acer rubrum.*
Variety denomination: 'Frank Jr.'

BACKGROUND OF THE INVENTION

Beginning in 1984, I planted a number of the cultivars of *Acer rubrum* together in J. Frank Schmidt, Jr. Arboretum in Boring, Oreg. As these grew, they began to cross pollinate and set seed. In the spring of 1992, I gathered seed from these trees that had fallen to the ground. As the seeds of these trees are wind dispersed samaras, it was not possible to determine which individual trees were the parents of each seed. These seed were planted in a nursery seedbed in Boring, Oreg., and quickly germinated. I planted out a number of the best seedlings in a nursery row in the spring of 1993 and grew them on to larger size. Over the 1994 and 1995 growing seasons, I evaluated these seedlings.

The original tree of my new variety was transplanted during the spring of 1996 into a long term trial block, where I continued my evaluation. I directed propagation of my new variety of tree on *Acer rubrum* rootstock for growing and further evaluation in J. Frank Schmidt & Son Co. nursery grounds in Boring, Oreg. and Canby, Oreg. Through this evaluation process, I determined that my new cultivar 'FRANK JR.' possessed a unique and valuable set of characteristics.

Subsequent asexual propagation under my direction by budding on *Acer rubrum* understock, by softwood cutting propagation, and by micropropagation have all shown that the characteristics of my new tree are firmly fixed in successive generations.

Classification: In recent years, some authors have reclassified some cultivars of *Acer rubrum* as the hybrid species *Acer×freemanii*. A few of the seed and pollen producing trees in the Arboretum that contributed to my seed supply could be classified by these authors as *Acer×freemanii*. There is not complete agreement on this issue among experts. My belief is that *Acer rubrum* and *Acer×freemanii* form a species complex with various degrees of genetic introgression. In this patent application, *Acer rubrum* is used in the broader, traditional sense. My new cultivar appears closest in characteristics to the species *Acer rubrum* and is thus classified.

BRIEF SUMMARY OF THE INVENTION

This new cultivar possesses a unique combination of characteristics in that it combines an upright pyramidal form with a strong straight central leader, dark green summer foliage, and bright red fall color.

BRIEF DESCRIPTION OF THE DRAWING

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
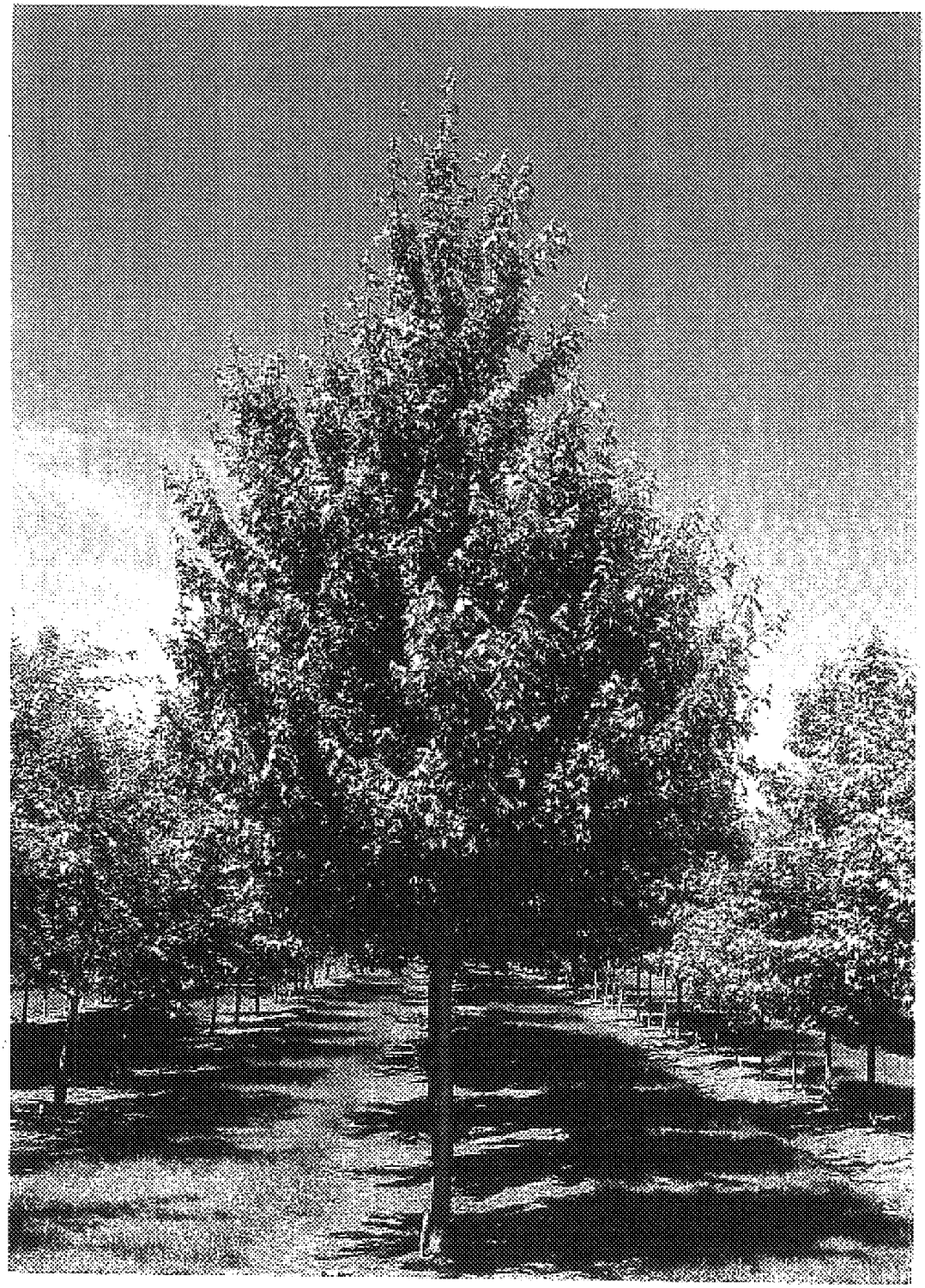
FIG. 1 illustrates the tree in summer (July), with the dark green foliage and upright pyramidal form.
Figure 2:
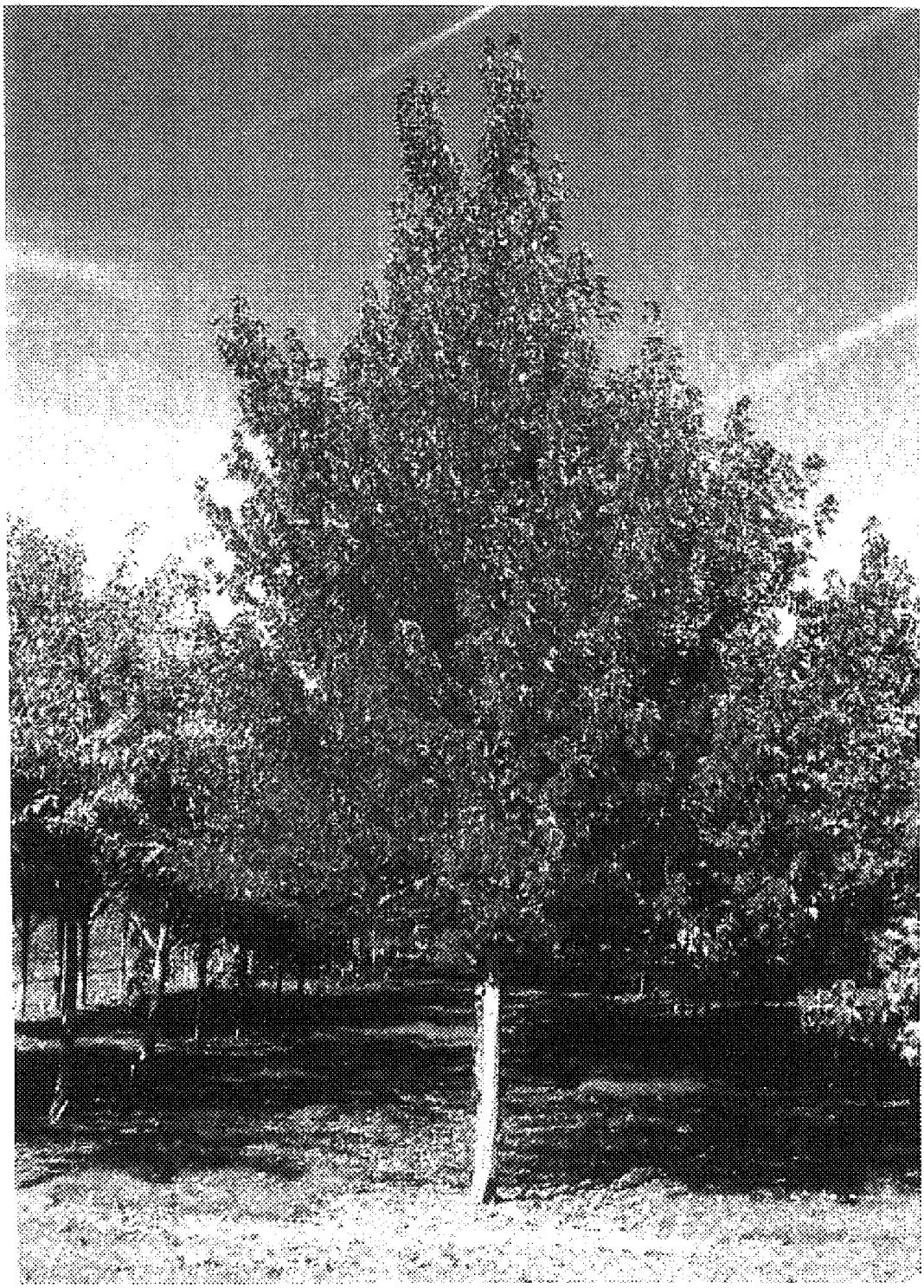
FIG. 2 illustrates the tree in October in fall color.
Figure 3:
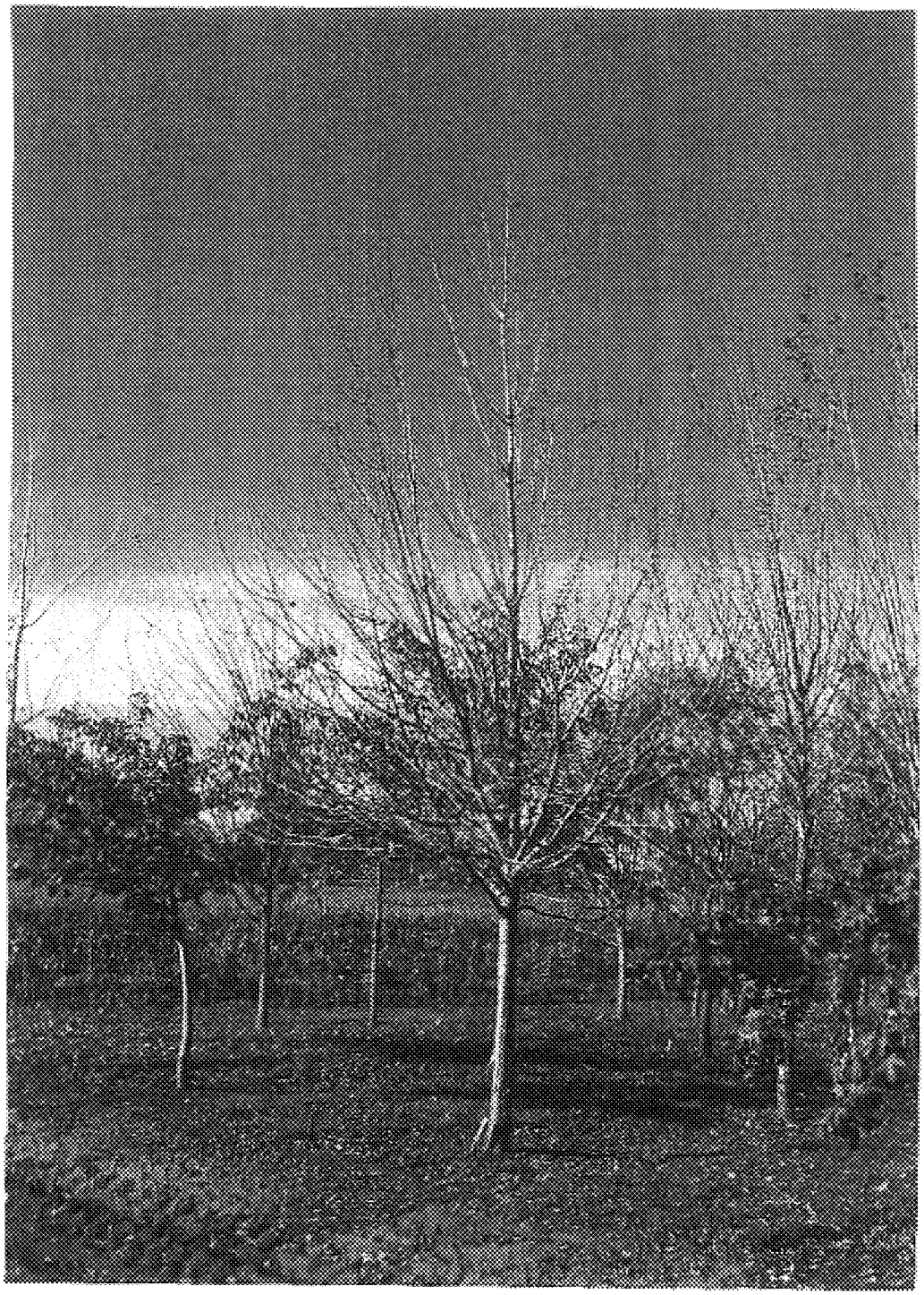
FIG. 3 illustrates the dormant tree in November, showing branching habit, pyramidal form, and dominant central leader.
Figure 4:
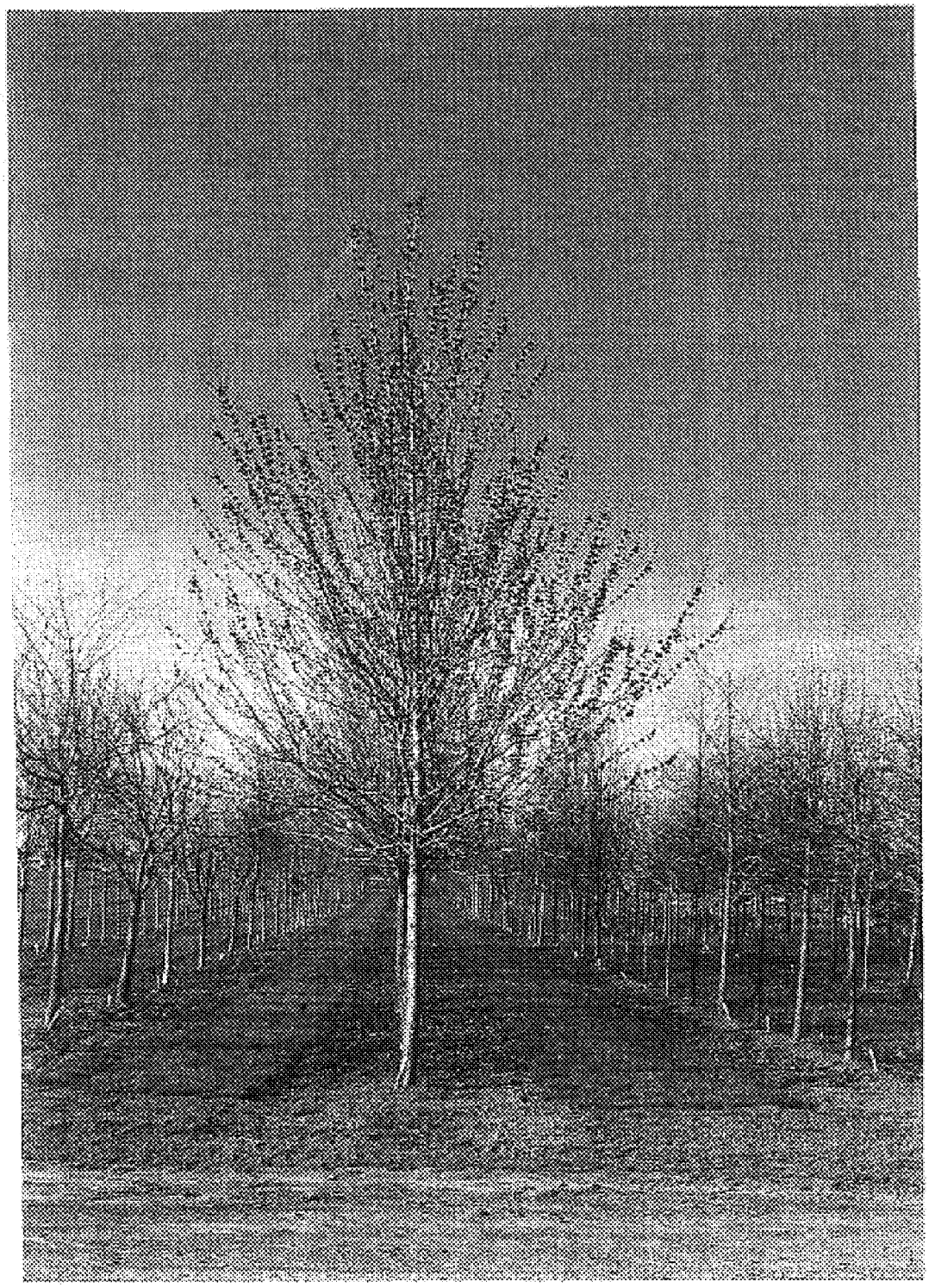
FIG. 4 illustrates the tree in March, in flower.
Figure 5:
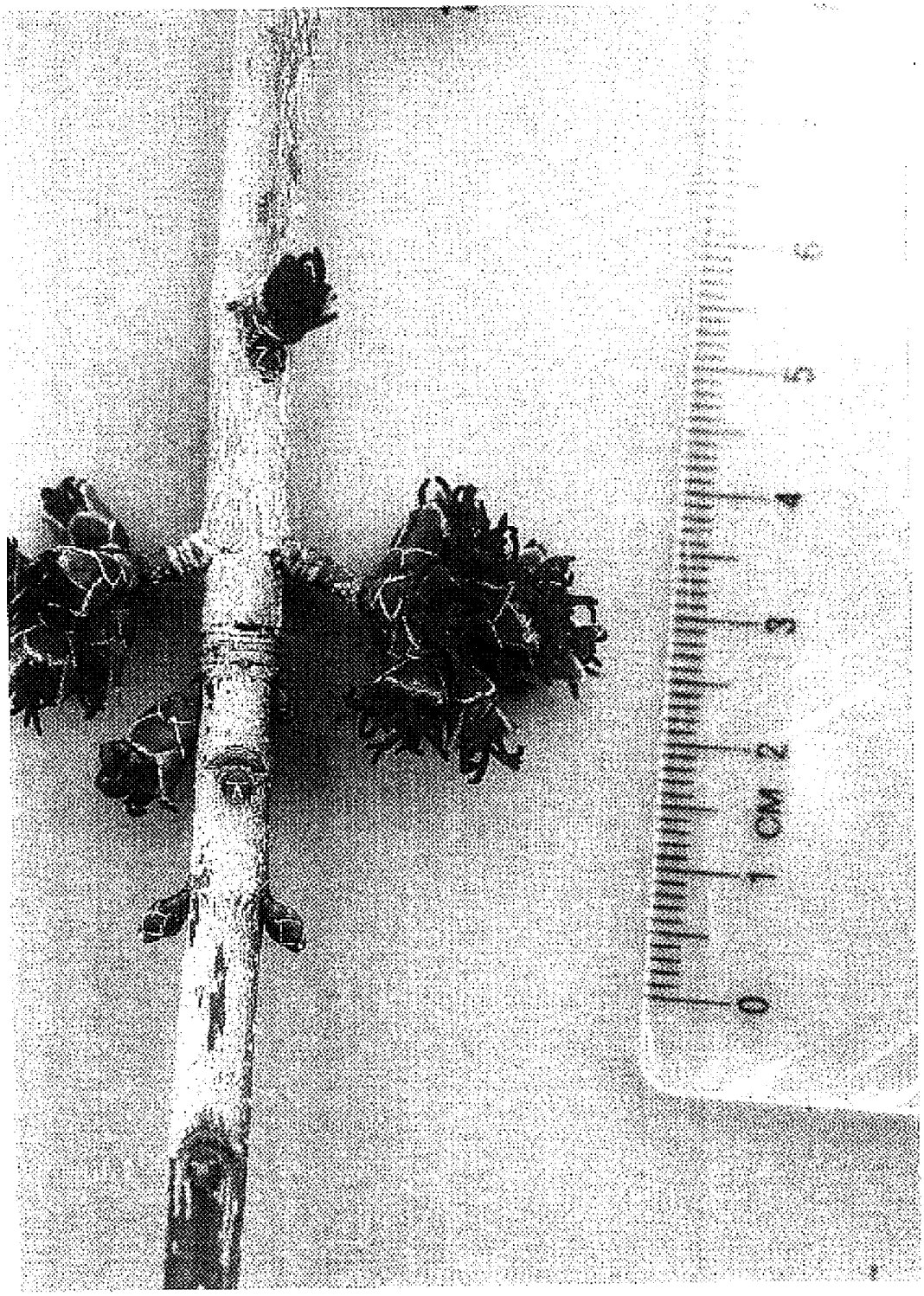
FIG. 5 is a close up of the flowers.
Figure 6:
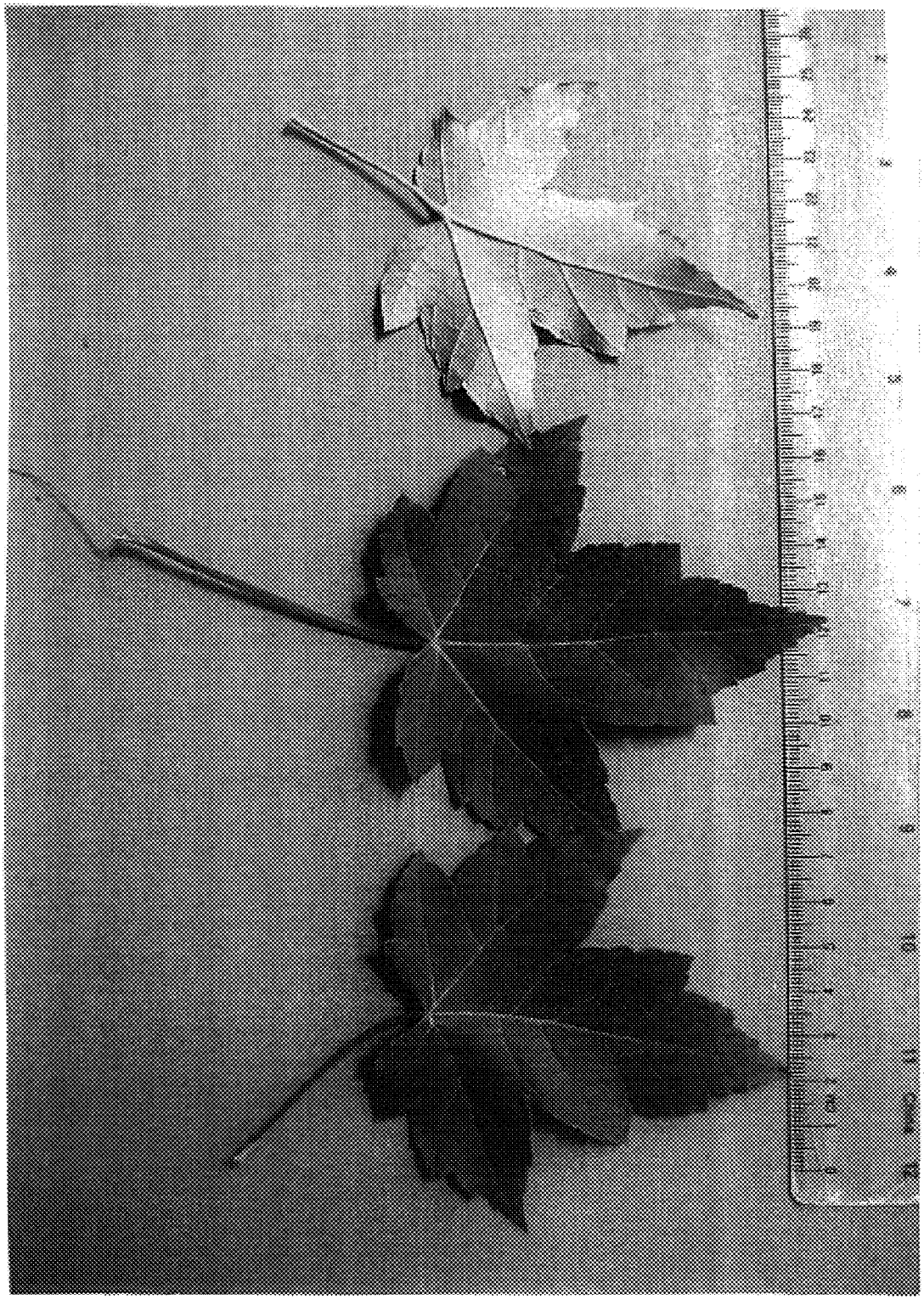
FIG. 6 is a close-up of summer foliage, showing typical leaf shape and color.
Figure 7:
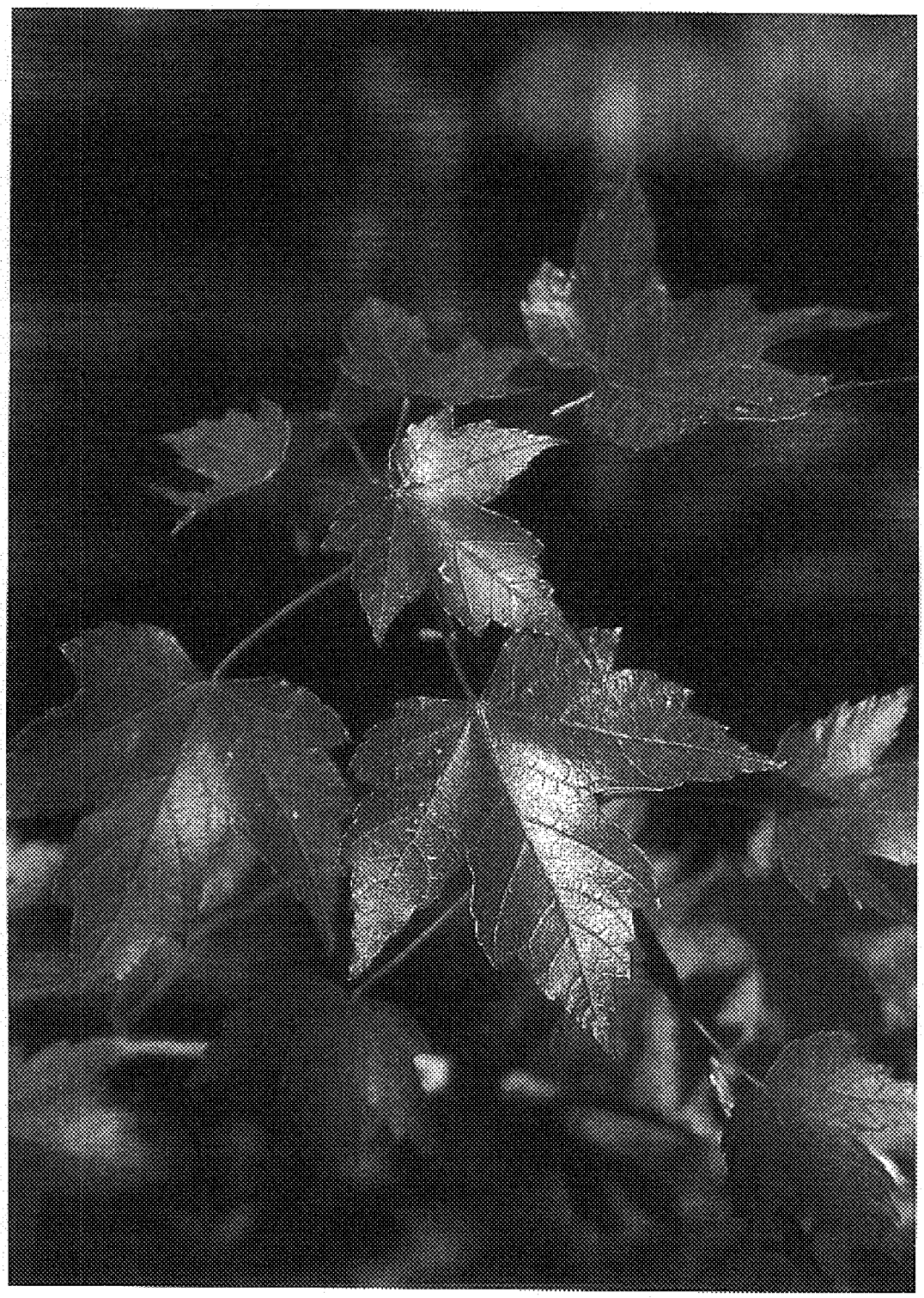
FIG. 7 is a close-up of some Fall foliage, showing peak fall color.
Figure 8:
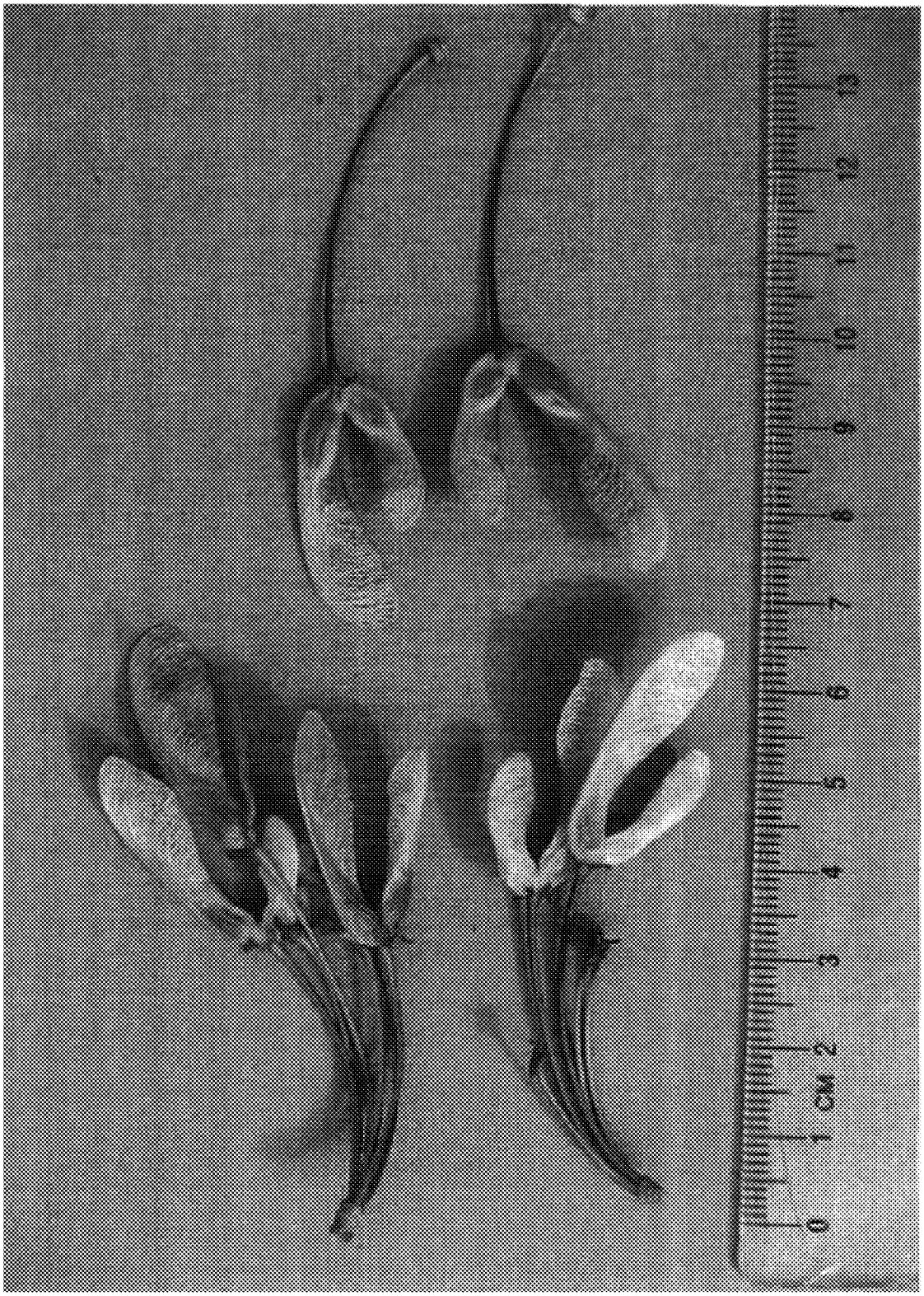
FIG. 8 is a close-up of some fruit (samaras) when ripe, taken in late April.

The following detailed description of the 'Frank Jr.' variety is based on observations of the original tree growing in Boring, Oreg. and of one and two year old asexually propagated progeny. The observed progeny were trees which were growing on *Acer rubrum* rootstock in Boring, Oreg. and in Canby, Oreg. All color references are based on The Royal Horticultural Society Colour Chart.

Scientific name: *Acer rubrum* 'Frank Jr.'.
Parentage: *Seed parent.*—Unknown, an open pollinated *Acer rubrum* seeding.
Tree: Unless otherwise noted, observations are from the original tree at about 10 years of age.

*Overall shape*.—Pyramidal with a strong central leader.

*Height*.—7.0 meters.

*Width*.—3.6 meters.

*Caliper*.—10.1 cm at 1 meter above ground.

*Trunk*.—Sturdy, round in cross section.

*Trunk bark texture*.—Smooth.

*Trunk bark color*.—Immature bark color: Greyed-green 197A to 197B. Mature bark color: Greyed-green 197B to 198D. Lenticels: None apparent.

*Primary branches*.—Sturdy, radiating outward and upward, symmetrically from the central trunk. Angle of attachment averages 70 degrees. Branch diameter measured 10 cm from trunk averages 27% of the diameter of the trunk, indicating good central dominance.

*Branch color*.—Greyed-orange 174D to 177A.

*Branch lenticels*.—Present on current season shoots, then becoming unnoticeable over the next two seasons as the bark ages. On current season shoots: 1–3 mm long×0.5 mm wide, color Yellow-white 158A.

*Dormant buds*.—Greyed-red 179A. Two buds per node, opposite. Ovoid, laterally flattened, 4 mm long×4 mm wide×2 mm thick.

*Internodes*.—Average length 7.2 cm.

*Hardiness*.—Based on limited freeze testing, mid-winter hardiness is believed to be USDA Zone 4.

*Disease resistance*.—Good resistance to *Pseudomonas syringae* leaf spot, based on field observations in Oregon.

*Insect resistance*.—Good resistance to two-spotted spider mite, based on field observations in Oregon.

Leaves: Except as otherwise noted, observations are averages from twenty typical vigorous growth leaves.

*Arrangement*.—Opposite.

*Texture*.—Smooth.

*Sheen*.—Very slight glossiness.

*Length*.—10.2 cm.

*Width*.—11.3 cm.

*Petioles*.—7.1 cm long×1.5 mm thick, Greyed-red 181A on the portions exposed to full sun, and Yellow-green 153A on the shaded portions.

*Overall shape*.—Palmate with three major lobes and two minor lobes, the minor lobes sometimes being missing.

*Margin*.—Irregularly serrate to crenate-serrate.

*Tip*.—Acute to acuminate.

*Base*.—Cordate.

*Stipules*.—None.

*Spring leaf color of first emerging leaves*.—Greyed-red 181A on first emerging. This color becomes an overtone, combined with Green 138A as leaves expand.

*Summer leaf color*.—Upper leaf surface: Green 131A to 139A. Lower leaf surface: Greyed-green 188B to 190B. Vein: Yellow-green 145B.

*Fall leaf color*.—Red 46A.

*Fall leaf color timing: Average of* 2003 and 2004 season dates in Boring, Oreg.:

*First autumn color*.—September 25 .

*Peak autumn color*.—October 9.

*Full defoliation*.—October 27.

*Pubescence*.—Leaves are glabrous above, sparsely pubescent on veins of underside with a few scattered dark brown thickened hairs on underside of leaf blade.

*Persistence*.—Tree is deciduous.

Flowers: Observations are from representative flower samples observed in Boring, Oreg.

*Overall*.—A small sessile umbel of five to six flowers, tightly held and surrounded by four bud scales, with the flower cluster appearing oval to urn shaped with flaring styles. The tree only produces pistillate (female) flowers.

*Shape*.—Individual flowers are flattened in one dimension with flaring styles.

*Size*.—Individual flowers are 4 mm wide×5 mm tall. The flower clusters are 6–7 mm in diameter.

*Flower buds*.—2 mm to 3 mm wide×4–6 mm long, ovoid.

*Color*.—Unopened buds: Greyed-purple 183A. Opened flower: The overall flower cluster appears Greyed-purple 183C to Greyed-purple 185A.

*Petals and sepals*.—Reduced to a series of five each, indistinguishable in appearance, rounded, each 1 mm high×1 mm wide, Red 53 A.

*Stamen*.—Nonfunctional and petaloid. Reduced to a series of generally six petaloid appendages on the flower inside of petals and sepals. 1 mm high×0.5 mm wide.

*Anthers*.—Non-functional, reduced to less than 1 mm, petaloid, Red 53A.

*Pistil*.—Style is short, 1–2 mm, then divides into two long stigmas, each 2–3 mm long×0.5 mm wide, velvety texture, Red-purple 185A.

*Pollen*.—None.

*Pedicel*.—Length: 2 mm. Width: 0.5 mm. Color: Yellow-green 144C when in first emerging, then changing to Greyed-purple 185A as flowers and seeds mature.

*Pubescence*.—Flowers are glabrous except stigmas which are velvety and flower bud scales which are tomentose, especially at the margins.

*Fragrance*.—None.

*Flowering date*.—Based on 2003 data, in Boring, Oreg. First bloom: February 25. Peak boom: March 10. End of bloom: March 16.

Fruit: Observations are from a sampling of typical fruit. The fruit is a samara, held in pairs by a pedicel in custers of four to six. The samara is attached at the seed end and the wings diverge at a 20 to 30 degree angle. The samaras are striated with a thickened keel on the outer edge with a thin and papery wing.

*Size*.—26 mm×8 mm×2 mm thick at seed end.

*Shape*.—Asymmetrically elongated with wing which becomes papery thin.

*Lenticels*.—None.

*Color*.—When first formed, samaras are Greyed-purple 185A. As they ripen, they turn to Greyed-orange 165C to 165D.

*Seeds*.—Oval, 5 mm×3 mm×1 mm thick, slightly pointed at the attachment end. Greyed-orange 174B to 166B.

*Fruit production*.—Sparse, few fruits produced, only sets seed in occasional years.

*Fruit maturity*.—Based on 2004 data, fruit matures and drops from tree April 30 to May 5.

*Usage*.—None.

Comparison to Other Varieties:

Compared to observed specimens of the popular cultivars 'Franksred' and 'Jeffersred' U.S. Plant Pat. No. 4,864, 'Frank Jr.' has a distinctly straighter central leader when measured on nursery grown two year old trees. The average measurements for the angle of deflection from vertical of the terminal 30 cm of the central leader of 10 trees each demonstrates this:

| | Central Leader Variance from Vertical |
|---|---|
| 'Frank Jr.' | 5.5 degrees |
| 'Franksred' | 14.1 degrees |
| 'Jeffersred' | 13.1 degrees |

Comparison to the parent species:

Growth rate: My new variety is significantly faster growing than typical *Acer rubrum*, growing to an average of 2.72 meters as a one year old tree in nursery conditions in Boring, Oreg., vs. 2.35 meters for *Acer rubrum.*

Crown form: My new variety develops an upright pyramidal form, while typical *Acer rubrum* trees are oval to rounded.

Straight leader: My new variety develops a very straight central leader, averaging 5.5 degrees variance from vertical measured on the top 30 cm of two year old trees, while typical *Acer rubrum* trees have leaders with an average variance from vertical 13.9 degrees.

Summer foliage: My new variety has summer foliage that is very dark green on the upper surface and light in color on the underside. Compared to observed specimens of *Acer rubrum*, 'Frank Jr.' has distinctly darker leaves, measured by the mid-summer upper leaf surface.

| | Upper leaf surface | Lower leaf surface |
|---|---|---|
| 'Frank Jr.' | Green 131A to 139A | Greyed-green 188B to 190B |
| *Acer rubrum* | Green 137A | Greyed-green 191A |

Fall foliage: My new variety has fall foliage color that is bright red, Red 46A. Typical *Acer rubrum* trees are variable in color, typically developing shades of yellow, orange, or red.

Flowers: Compared to observed specimens of *Acer rubrum*, the flowers of 'Frank Jr.' has distinctly short pedicels and styles.

| | Pedicel | Style |
|---|---|---|
| 'Frank Jr.' | 2 mm | 1–2 mm |
| *Acer rubrum* | 4 mm | 5 mm |

I claim:

1. A new and distinct variety of Red Maple tree, substantially as herein shown and described.

* * * * *

UNITED STATES PATENT AND TRADEMARK OFFICE

CERTIFICATE OF CORRECTION

PATENT NO. : PP 16,769 P2
APPLICATION NO. : 11/083834
DATED : July 4, 2006
INVENTOR(S) : Keith S. Warren It is certified that error appears in the above-identified patent and that said Letters Patent is hereby corrected as shown below:

Col. 4, line 42, please replace “pedicel in custers” with the phrase --pedicel in clusters--.

Col. 5, line 17, please replace “vertical 13.9” with the phrase --vertical of 13.9--.

Col. 6, line 9, please replace “has distinctly” with the phrase --have distinctly--.

Signed and Sealed this

Fourteenth Day of November, 2006

JON W. DUDAS
*Director of the United States Patent and Trademark Office*